United States Patent [19]

Swidler et al.

[11] 4,150,020
[45] Apr. 17, 1979

[54] REACTIVE XYLYLENE DIPHOSPHONIC ACID DYES

[75] Inventors: Ronald Swidler; William A. Sanderson, both of Palo Alto, Calif.

[73] Assignee: Burlington Industries, Inc., Greensboro, N.C.

[21] Appl. No.: 860,115

[22] Filed: Dec. 13, 1977

Related U.S. Application Data

[60] Continuation of Ser. No. 602,013, Aug. 5, 1975, abandoned, which is a division of Ser. No. 534,349, Dec. 18, 1974, abandoned, which is a continuation-in-part of Ser. No. 441,393, Feb. 11, 1974, abandoned, which is a continuation-in-part of Ser. No. 260,587, Jun. 7, 1972, abandoned.

[51] Int. Cl.² .................... C09B 62/80; C09B 62/82; D06P 1/384; D06P 3/10
[52] U.S. Cl. .................................. 260/163; 260/153; 260/178; 260/184; 260/191; 260/197; 260/198; 260/199; 260/200; 260/201; 260/206; 260/307 G; 260/374; 260/377; 260/378; 260/380
[58] Field of Search ............... 260/163, 197, 198, 199, 260/200, 201, 374, 191

[56] References Cited

U.S. PATENT DOCUMENTS

| | | | |
|---|---|---|---|
| 3,232,927 | 2/1966 | Randall et al. | 260/163 |
| 3,301,846 | 1/1967 | Chiddix et al. | 260/163 |
| 3,339,999 | 9/1967 | Wick | 8/34 |
| 3,947,435 | 3/1976 | Pechmeze et al. | 260/190 |

Primary Examiner—Floyd D. Higel
Attorney, Agent, or Firm—Cushman, Darby & Cushman

[57] ABSTRACT p-Xylylenediphosphonic acid groups connected through the aromatic ring to a variety of chromophores provide a class of novel dyes of the general formula

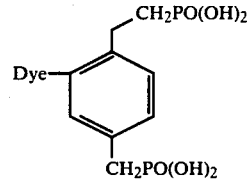

wherein "Dye" represents the chromophore. These dyes may be covalently bonded to fibers and other substrates containing hydroxyl, amino, or thiol groups to form phosphonic acid esters or amides by reaction in the presence of a carbodiimide such as cyanamide or dicyandiamide.

7 Claims, No Drawings

REACTIVE XYLYLENE DIPHOSPHONIC ACID DYES

CROSS REFERENCE TO RELATED APPLICATIONS

This is a continuation of our application Ser. No. 602,013 filed Aug. 5, 1975, which in turn is a division of our application Ser. No. 534,349 filed Dec. 18, 1974, which in turn is a continuation-in-part of our application Ser. No. 441,393 filed Feb. 11, 1974, which in turn is a continuation-in-part of our application Ser. No. 260,587 filed June 7, 1972, all of which are now abandoned.

BACKGROUND OF THE INVENTION

1. Field of the Invention

The present invention relates to dyeing of fibers and more particularly to reactively dyed fibers in which a chromophore is linked through a condensation residue to sites on the fiber.

2. Description of the Prior Art

Dyes are retained in fibers by physical adsorption, salt or metal-complex formation, solution, mechanical retention, or the formation of covalent chemical bonds. Physical adsorption and solution, in which the dye is partitioned between the fiber and the surrounding aqueous phase, are equilibrium reactions, and only by very careful selection of the dyes used, can good washfastness properties be achieved. Salt and metal complex formation are also equilibrium reactions and, though generally the retention of the dye is favored more than in physical adsorption, washfastness may still present a problem. The dyes that are held by mechanical retention (azoics, vats and sulfurs) are virtually insoluble in water and show excellent fastness to washing, but have other disadvantages. They are, for example, difficult and expensive to apply; loose dye, which is not easily washed off, may be deposited on the surface, resulting in low fastness to rubbing (crockfastness), and the final shade of the dyeing does not develop until completion of the whole dyeing cycle and after treatments.

Chemical bonding of dye to fiber for fixation of dye was recognized as early as 1895. The reactive dye systems presnetly available require that the dyes contain a functional group capable of forming a covalent chemical bond with the fiber.

Fiber-reactive dyes are employed quite widely in coloring cellulosics and proteinaceous fibers. They, of course, exhibit excellent washfastness, resistance to rubbing, tinctorial powers, ease of application and leveling. The latter quality is a measure of uniformity and most important for long dye runs and color matching. Inasmuch as one can prepare either fiber substantive or non-substantive dyes, direct application to precision printing becomes a feasible and functional commercial operation. The reaction of the dye with cellulosic fibers is basically an etherification reaction and is broadly espresented as:

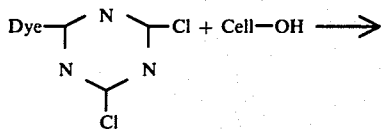

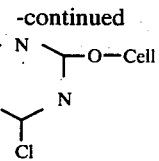

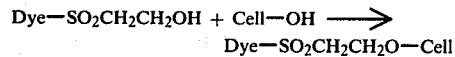

The triazine reactive group imparts oil solubility characteristics to the high molecular weight dye which hinders and interferes with an aqueous solublizing group such as —$SO_3H$. These dyes are unstable and difficult to work with. Most of the reactive dye systems are based upon chemistry where the reaction is effected in alkaline solutions. There are few present reactive dye systems which operate effectively in an acid pH. Such a system is desirable in the dyeing of mixed fabrics such as cotton blends with polyester, wool or nylon, the latter fibers being dyeable by acid dyes. However, acid dyes generally have no affinity for cellulose and usually only find use in dyeing of proteinaceous fibers. Furthermore, since the dye and fiber substrate are coreactive, complete dyeing of the fabric will occur unless special precautions are practiced to localize the dye in areas of the fabric by printing, stenciling or other graphic technique.

The American Cyanamid Company has published a booklet entitled "Cyanamide", wich sets forth a considerable number of reactions of cyanamide and dicyandiamide. Page 32 of this booklet indicates that cyanamide was long known to be a dehydrating agent when warmed with anhydrous formic acid and in the esterification of lactic or salicylic acid in absolute ethanol. Note Pratorius-Seidler; G., J. prakt. Chem. [2] 21, 129–50 (1880); C.Z. 1880, 245. A number of papers have investigated the reaction of cyanamide with carboxylic acids, and have proposed a mechanism wherein the acid is converted to the anhydride by interaction with cyanamide, with formation of urea, and subsequent acylation of the urea by the anhydride to produce a ureide, which at elevated temperatures interacts with the acid to produce an amide. Cyanamide and dialkylcyanamides are also useful in the synthesis of pyrophosphates. Kenner, G. W., Reese, C. B., and Todd, A.R., J. Chem. Soc. 1958, 546–51; C.A. 52, 11072 (1958) indicates that a high energy phosphorous-oxygen bond is present in the presumed intermediate O-phosphorylpseudourea.

The use of cyanamide and phosphoric acid to impart flame retardant properties to cotton and other cellulosic fabrics is well known to the art. For instance, O'Brien "Cyanamide Based Durable Flame-Retardant Finish for Cotton", Textile Research Journal, March, 1968, pp. 256–266 indicates, at page 265, that the reaction of cyanamide and phosphoric acid with cellulose results in a cross-linking of cellulose molecules. From the properties of the resulting product, it is suggested that the cross-linked cellulose is some type of a dicellulose phosphate ester.

SUMMARY OF THE INVENTION

The present invention provides a dye system for dyeing hydroxy substituted substrates in which the reaction can be conducted in acidic to mildly alkaline solutions. The dye system of the invention is a reactive system in which the reactive function is not self-contained in the dye molecule. Since the dye and fiber require the presence of a condensation agent for reaction, certain dyes such as azo dyes, where the dye is formed by a simple coupling reaction, can be formed via an intermediate on the fabric which can be selectively color developed in discrete locations to form a pattern. The background areas can be fixed to expose or decompose the remaining precursor areas. The dye system of the invention is further simplified in that a single group serves both as an aqueous solublizing group and as the potentially reactive coupling site to the fiber, thus providing a more simplified synthesis and a less complex and more stable dye molecule and dyed fabric.

The dye system of the invention results in reactively dyed fabrics by immobilization of a dye as a cellulose phosphorous ester according to the following illustrative reaction:

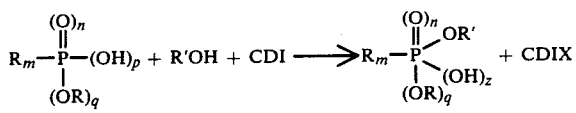

where R is a chromophore, R'OH is cellulose, DCI is a carbodiimide. CDIX is a CDI residue or by-product, m is 0, 1 or 2, n is 0 or 1, p is 1 or 2, q is 0 or 1 and $z = p-1$.

Thus, a chromophoric grouping (R) linked chemically to a phosphorus acid such as phosphonic, phosphonous, phosphinic or phosphoric acid, reactively dyes cellulose (R'OH) with the aid of a carbodiimide condensing agent (CDI). Cyanamide which is a suitable carbodiimide, allows for a rapid esterification of phosphorus acids with alcohols. The byproduct, CDIX, is urea. Thus, where R is a chromophore and R'OH is cellulose, a fiber reacted dye compound is formed with cellulose. This results in a substantial and washfast dyeing of cotton and other cellulosic or hydroxy containing substrates. Cellulose esters of phosphonic acid dyes are found to be the most stable to heavy-duty alkaline detergents. The reaction of phosphonic acid dyes would proceed as follows:

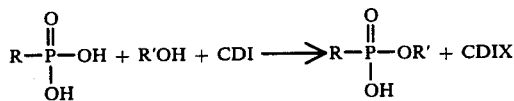

The fabric or fiber system of the invention proceeds by forming an aqueous solution of a chromophore or precursor thereof linked chemically to a phosphorus containing acid. The solution generally contains at least 0.1% of the dye and generally no more than 10% by weight of the dye depending on the intensity of the chromophore and the shade desired. The dye concentration is generally between 0.1 and 5% by weight and the concentration of reacted dye on the fabric is believed to be in the range of 0.01 to 0.05 weight percent, although much greater concentrations of dye on the fabric can be employed, e.g., up to even 5.0 weight percent, or more; $10^{-4}$ to $10^{-2}$ mol. percent.

The pH of the solution is generally about 3-4 but can be varied from about 1.5 to 9. Lower pH's can be provided by addition to the impregnation bath of a 1-5% of an acid which is non-volatile at the cure temperature, and does not cause undue degradation of the substrate, such as a phosphoric acid, llower alkyl phosphonic acid or chloroacetic acid. This appears to improve the efficiency of the dye immobilization since less dye is found to wash out after cure. The amount of carbodiimide is usual increased in a bath containing added acid. Higher pH baths may be utilized containing salts which are converted to the acid form during cure such as fugitive amino salts, or ammonium salts of the phosphorus acid chromophore. Higher pH baths may be necessary in certain situations which present corrosion problems, mixed fiber systems or fibers which would be excessively degraded at low pH.

Generally, in the bath the equivalent ratio of the diimide to the phosphono function is at least about 2:1. Curing is generally conducted at a temperature of at least 200° F and generally below 400° F. Optionally, the fabric may be preliminarily dried at a temperature below 200° F before cure. The cure time can be varied from the order of seconds to hours depending on the temperature, dye concentration and fiber being colored.

The reactive dye system of the invention is generally applicable to substrates containing available hydroxyl groups such as cellulose, particularly cotton and may be practiced on fibers, films, yarns, cords, threads, paper, fabrics, non-woven or woven, knitted; or other types including pile fabrics, velvets, knitted fabrics, corded webs or webs formed by a random webber.

The water-soluble condensation agent assists in the formation of the ester linkage between the chromophore, R, and the cellulose substrate, R'OH. The agent is preferably a water soluble carbodiimide such as cyanamide or dicyandiamide.

The impregnating bath may also contain minor amounts of conventional additives or assistants such as anti-migrating agents such as Glauber's salt, or wetting agents. Compatible thickeners may also be present.

The dyes that can be utilized in the dye immobilization process of the invention can be of diverse type and structure. The dye may be an anthraquinone, phthalocyanine, mono-azo, polyazo, benzanthrone, pyrazolone, naphthoquinone, triarylmethane or cyanine type that is modified to contain a phosphorus acid group to impart water-solubility and to provide a reactive site for attachment to the hydroxyl atoms on the substrate. The dyes may contain other aqueous solubilizing groups such as sulfonate and may contain other substituents that do not interfere with aqueous solubility characteristics or the dye immobilzation esterification reaction.

Many of the phosphorus acid substituted dyes utilized in the process of the invention are known materials readily available in the art, and have been used to direct dye wool and other proteinaceous fibers. Suitable dyes are disclosed in Belgium Pat. No. 570,326, British Pat. No. 455,092 and U.S. Pat. Nos. 2,596,660 and 2,799,701, the disclosures of which are incorporated herein by reference. Analogues of sulfonated dyes can readily be synthesized in the phosphono form by substituting the phosphono analog for the sulfono containing compound during synthesis.

The process of the invention may be readily adapted so that it can be carried out in commercially available machinery used for dyeing or textile printing processes and for continuous or non-continuous variations of such processes. The fibrous or sheet material may be impregnated with the dyestuff solution and then subjected to curing by heating, for example, in a hot flue dryer, an oven or a stenter. The impregnation may be carried out for example by padding material with an aqueous solution containing the dyestuff and curing agent. The dye treatment may also be carried out by textile printing methods, for example, by locally treating the textile with a solution containing the dyestuff and condensation agent and thereafter subjecting the printing material to an elevated temperature for curing. Alternatively a phosphono-substituted primary agent may be coupled to the cellulose and thereafter coupled to an azo chromophoric component.

The invention will now become better understood by reference to the following detailed description when considered in conjunction with the specific examples of practice. It is to be understood that these examples are presented solely for purposes of illustration and not by way of limitation and alternative materials may readily be substituted without departing from either the spirit or scope of the invention.

DESCRIPTION OF THE PREFERRED EMBODIMENTS

The following example illustrates the synthesis of a phosphono analog of Yellow No. 1, a pyrazolone dye:

EXAMPLE 1

8.7 grams of 3-phosphanilic acid and 5.3g of $Na_2CO_3$ were added to 100 ml of $H_2O$ and cooled to 15° C. 3.7g of $NaNO_2$ in 10 ml of $H_2O$ were added to yield a brown solution which was slowly poured with stirring onto 21 ml of concentrated HCl containing 60g of ice. The mixture was stirred for fifteen minutes and gave a positive response to the starch - KI test.

The diazotisation method is based on Vogel, "Practical Organic Chemistry" (1951), p. 596, the disclosure of which is incorporated herein by reference, and follows the following reaction sequence:

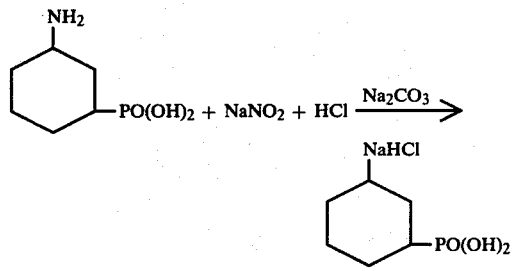

III

Coupling of the diazotized intermediate (III) is based on British Pat. No. 753,771. The solution containing the intermediate (III) was added to a solution containing 12.7g (1/20 mole) of 3-methyl-1-(p-sulfophenyl)-2-pyrazolin-5-one and 10g of sodium acetate in 100 ml of $H_2O$. The pH of the second solution had been adjusted from 5.3 to 7.0 with NaOH. After stirring for fifteen minutes the pH was 2.0 and there was no evidence of precipitation. On addition of isopropanol, a yellow powder was precipitated which after separation and drying in a vacuum oven yielded 13g. Coupling proceeded according to the following reaction:

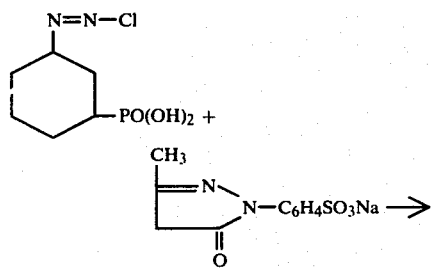

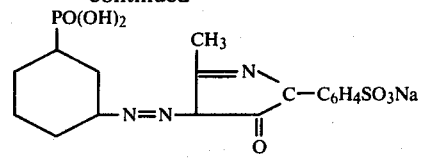

The following example illustrates the synthesis of a bis phosphono; bis-azo dye.

EXAMPLE 2

3-phosphanilic acid was diazotized according to the procedure of Example 1 using 13 ml of concentrated HCl. 18.0g (1/20 mole) of the mono-sodium salt of 8-amino-1-naphthol-3,6 -disulfonic acid was suspended in 50 ml of $H_2O$ and the pH was adjusted from 2.3 to 7 with NaOH. This solution was added to the diazotate to form a dark red solution having a pH of 2.5.

Alkaline coupling was practiced according to Vogel, supra, p. 597, the disclosure of which is incorporated herein by reference.

The red solution precipitated on standing and was adjusted to pH 7 with NaOH. 40 ml of a 10% NaOH solution was then added and cooled to 5° C. A second preparation of diazotate was then added to form a blue solution having a pH of 7.4. After fifteen minutes the pH was adjusted to a pH of 2 with HCl. The dye was precipitated with isopropanol to yield 40 grams of black powder having the formula:

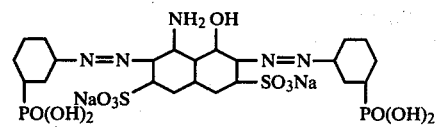

The pyrazolone yellow dye of Example 1 was used to dye cotton fabrics according to the following procedure.

EXAMPLE 3

A pad bath was prepared containing 5% of the pyrazolone yellow dye, three equivalents of cyanimide (1.33 weight percent) and 0.1% Triton X 100 (Rohm & Haas - octyl phenoxy polyethoxy ethanol — non-ionic wetting agent). The bath had a pH of 2.9. Samples of print cloth fabric were padded at 40 psi, and then oven dried for five minutes at 150° F except for one fabric that was air dried at room temperature. One sample of fabric was cured for five minutes at 320° F. An oven dried fabric was cut in half for color comparison. All but one one-half of the oven dried fabric was washed for eight minutes with heavy-duty detergent, dried and then ironed. The air-dried fabric was colorless, the oven dried fabric was colorless whereas the cured fabric had a bright lemon yellow color with some washoff by comparison with unwashed. The colored fabrics were boiled for one hour in 3% $K_2CO_3$ with some color lost. The final color was a pastel yellow shade of the original bright yellow color.

Since the fabric subjected to air drying lost all color on washing, it is apparent that the dye was not substantive. It is qite unexpected that the ester linkage of the fixed dye is stable to hot detergent alkaline medium since it would be expected that the phosphorus ester moiety would hydrolyze and rupture the dye attachment.

The blue dye of Example 2 was utilized to color cotton fabric according to the following procedure:

EXAMPLE 4

A pad bath was prepared containing 5% of the blue dye plus 6 equivalents of cyanamide (1.73%) and 0.1% of Triton X 100. The pH of the bath was 2.6. Samples of cotton fabric were treated, dried and cured as in Example 3. After washing, the air-dried fabric was almost colorless. The oven dried fabric was a very pale blue whereas the cured fabric was a very dark navy blue. There was some slight washoff by comparison with the unwashed fabric. The warp shrinkage was $-3.75\%$ whereas the fill shrinkage was $+0.75\%$. After the fabric was boiled for one hour in 3% $K_2CO_3$m the final color was a dark purple.

It was then attempted to fix the dye of Example 1 on fabric using heat without the presence of a carbodiimide.

EXAMPLE 5

A bath was prepared, containing 5% by weight of the pyrazolone yellow dye of Example 1, plus 0.1% Triton X 100. The pH of the bath was 2.9. The bath did not contain any carbodiimide or equivalent material.

Samples of cotton fabric were padded at 40 psi, dried for five minutes at 150° F and cured for five further minutes at 320° F, washed in heavy-duty detergent and ironed. The fabrics contained only a trace of yellow color. A dye and heat step at curing temperature is not capable of fixing the dye on the fabric.

It was then attempted to fix on fabric the dye of Example 1 by means of a pad bath containing urea.

EXAMPLE 6

A bath was prepared 5% by weight of the pyrazolone yellow dye of Example 1, 0.1% Triton X 100 and 1.9% urea (3 equivalents). The pH of the bath was 2.9.

Samples of cotton fabric were treated as in Example 5 and the samples retained no more color than those of Example 5 showing that no dye immobilization occurred by this procedure.

It was then attempted to fix the dye of Example 2 on fabric using heat or urea in the absence of a carbodiimide.

EXAMPLE 7

Two baths were prepared, one containing 5% of the blue dye of Example 2 plus 0.1% Triton X 100 and the other additionally containing 2.5% urea (6 equivalents). The pH of the first bath was 2.65 and that of the second bath with urea was 2.70. Samples of cotton fabric were padded at 40 psi, dried for five minutes at 150° F, cured for five minutes at 320° F, washed in heavy-duty detergent and ironed. Only a trace of blue remained in the fabrics. Colors were all about the same.

The following example shows the use of polyvinyl alcohol and phosphoric acid as adjuvants to the coloring bath:

EXAMPLE 8

A pad bath was prepared containing 1% by weight of the blue dye of Example 2, 1% $H_3PO_4$, 1.6% cyanamide and 6 milliliters of 4% polyvinyl alcohol. No wetting agent was added. The pad bath was used to tread 100% cotton cloth and 50—50 cotton polyester cloth, according to the procedure of Example 3. The cloths showed good color retention and stability with very little washoff and very good resistance to boiling $K_2CO_3$. A similar bath containing 4% Cellosize in place of polyvinyl alcohol gave a similar result and also imparted some blue color to glass cloth.

The following example illustrates the use of dicyandiamide in place of cyanamide.

EXAMPLE 9

A pad bath was prepared containing 1.5% by weight of the yellow dye of Example 1 and 1% of dicyandiamide. (0.8% would be a ratio of 1:3.) Samples of cotton cloth were treated according to the procedure of Example 3. After washing, the dye immobilization was essentially the same as the cyanamide treated fabrics of Example 3.

The following example illustrates preparation of the benzyl phosphonic analog of the dye of Example 1.

EXAMPLE 10 p-Aminobenzyl phosphonic acid was coupled with the sulfophenyl pyrazolone utilized in Example 1 utilizing 9.4 grams of the benzyl acid (0.1 mole) in place of 8.7 grams of the phenyl acid. The pH was finally adjusted to 3.0 with HCl and the solid precipitated with isopropanol, presumably as the monosodium salt having the structural formula:

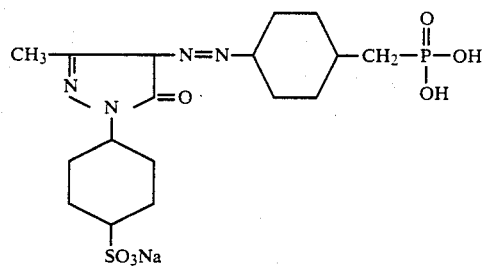

The dye exhibited similar behavior when utilized to color cotton fabric samples according to the procedure of Example 3.

The following experiment illustrates the preparation and use of the ammonium salt of the dye of Example 1 at higher pH.

EXAMPLE 11

An ammonium salt of the yellow dye of Example 1 was prepared by dissolving the dye in an aqueous $NH_4OH$ solution and evaporation the solution to dryness.

A pad bath was prepared containing 1% of the ammonium salt dye, 0.3% cyanamide and 0.25% Alipal CO 436 (nonyl phenoxy polyethoxy ethanol-sulfated, $NH_4^+$ salt). The pH of the bath was 5.8. The bath was applied to fabric and cured as in Example 3. The dye immobilization was substantially the same as in Example 3.

EXAMPLE 12

An acid pad bath was prepared containing 1% of the sodium salt of the phenyl dye of Example 1, 0.25% of Alipal and 3% of $H_3PO_4$ and 4.5% of cyanamide which represented an equivalent ratio of (1:3) of the cyanamide to the dye and acid. The pH of the pad bath was 1.8.

Samples of fabric cloth impregnated, cured and washed according to the procedure of Example 3 showed very little washoff. U.V. analysis of the cloth indicated about 75% dye fixation.

EXAMPLE 13

Methyl phosphonic acid (MPA) was substituted for the $H_3PO_4$ of the Example 12 and the cyanamide content was reduced by 1.3% to adjust the MPA/cyanamide equivalent ratio to 1:2. The pH of the bath was 1.8. Samples of fabric, impregnated, cured and washed according to the procedure of Example 3 again demonstrated very little washoff. A sample of fabric which was air-dried before cure to minimize migration showed somewhat improved color retention.

The following experiment shows the necessity of a phosphorus acid group in the dye molecule.

EXAMPLE 14

A pyrazolone dye was prepared utilizing m-sulfanilic acid in place of the m-phosphanilic acid of Example 1. A bath was prepared containing 1% of the sulfonated dye, 3% $H_3PO_4$, 0.25% Alipal and 4.5% cyanamide. The pH of the bath was 1.75. Samples of fabric impregnated, cured and washed according to the procedure of Example 3 showed extreme washoff demonstrating that little or no dye was fixed.

Fixation and immobilization of dye by formation of a phosphorus acid ester linkage was further confirmed by the following experiment.

EXAMPLE 15

A solution of 5% m-phosphanilic acid containing 3 equivalents of cyanamide was utilized to impregnate cotton cloth. The cloth was cured at 320° F for five minutes to couple the amine base to the cellulose through the phosphono-linkage.

The cellulose-coupled amine base was then subjected to diazotization with the $NaNO_2$-HCl solution of Example 1 to form a diazonium salt. A portion of the cloth was exposed to light to decompose the diazonium salt. The fabric was then immersed in a solution of the sulfophenyl pyrazolene utilized in Example 1 and dried and washed. Color was only retained in the nonexposed areas confirming the phosphono-ester linkage as the immobilization mechanism.

EXAMPLE 16

A copper phthalocyanine substituted with phosphonic acid and sulfonic acid groups was prepared by heating an intimate mixture of triammonium 4-sulfophthalic acid (11 g), monopotassium 4-phosphonophthalate (11 g), urea (20 g), cupric chloride dihydrate (3 g), and ammonium molybdate (0.25 g) at 250° C. The product was purified by washing with hydrochloric acid and drying in a vacuum oven at 60° C.

A bath was prepared containing 1% of this product, 1% $H_3PO_4$, 4.4% cyanamide and 0.25% Alipal. The pH of the bath was adjusted to 2.5 with triethanolamine. Samples of fabric impregnated, cured and washed according to the procedure of Example 3 were a greenish-blue color.

The present invention provides a novel acid system for the fast dyeing of hydroxy fibers. The reactively dyed fibers exhibit good color and are stable to hot basic media. The dye system of the present invention provides a further advantage since the dye can be recovered from the bath by precipitation on a calcium substrate such as lime, $CaCO_3$ or marble and can be regenerated by acid.

The results obtained hereinabove indicate that the process of reactively dyeing textiles and other substrates has broad applicability. The process of the present invention may be broadly applied to many substrates having an active hydrogen atom according to the well-known Zerewitinoff test (J. Am. Chem. Soc., 49, 3181 (1927)). Especially preferred are substrates having alcoholic hydroxyl (non-phenolic) groups, amino groups, or thio groups. That is, the reactive site on the substrate may have the formula —OH: —NH$_2$(amino); —NH-(amino); or —SH. Thus the process of the present invention results in the fixation of phosphrous-containing dyestuffs on rayon. The fixation is obtained with wool but the depth of shade is not as good as with rayon. Fixation of the dyestuff is also obtained with nylon, but the depth of shade is somewhat inferior to that of wool. Of the substrates having Zerewitinoff-active hydrogen atoms, those compounds having hydroxyl groups are greatly preferred, especially organic polymers having hydroxyl groups. While the sustrate may be in the form of cast or other massive articles, it is greatly preferred that the substrate be a textile fabric or a textile yarn, filament or fiber.

The results obtained with cyanamide and dicyandiamide suggest that cyanamide compounds of the general formula

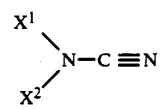

wherein $X^1$ and $X^2$ are hydrogen, lower alkyl, or together are

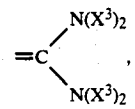

wherein each $X^3$ is independently hydrogen or lower alkyl, can be used in the process of the present invention. Thus, methylcyanamide, dimethylcyanamide, ethylcyanamide, diethylcyanmide, butylcyanamide, dibutylcyanamide, and other cyanamide compounds falling within the scope of the above formula disclosed in the aforesaid American Cyanamid Company "Cyanamide"booklet, the disclosure of which is hereby incorporated by reference, may be used in place of cyanamide or dicyandiamide Compounds of the above general formula may exist in tautomeric form and these tautomers are intended to be included in the general formula.

The dye, the fiber, and the cyanamide compound can be brought together in any particular order. Normally, the dye and the cyanamide compound, together with any conventional additives or assistants, will be in the form of an aqueous solution, which is padded or otherwise applied to the substrate. At least a coloring amount of the dye will be reacted onto the substrate.

As discussed hereinabove, it is possible to form the dyestuff on the fabric essentially "in situ", by coupling a phosphono-substituted compound to the cellulose and thereafter coupling that compound to an azo chromophore component or other chromophoric group. Alternatively, the phosphorus-containing dyestuff could be applied to a textile fabric which is then subjected to an after tratment with the cyanamide compound. Regardless of the technique actually used, it is clear that the thrust of the present invention resides in contacting a polymeric substrate containing Zerewitinoff-active hydrogen atoms, especially alcoholic hydroxyl, amino, or thio groups, with a cyanamide compound and with a chromophore-substituted phosphorus acid or a chromophore precursor-substituted phosphorus acid, and heating the contacted substrate to an elevated temperature to fix the chromophore or chromophore precursor to the substrate.

Mixtures of substrates, dyes, and/or cyanamide compounds may be used if desired.

The addition of phospheric acid to the impregnating bath appears to improve the efficiency of the dye immobilization, but has the undesirable effect of reducing the strength of the fabric by about 50%. Dyes containing two phosphonate groups or other phosphorus acid groups have been found to have an efficiency of greater than 90%, when affixed to cotton or another suitable substrate by the use of cyanamide or dicyandiamide, without using any phosphoric acid in the dyebath. Since no phosphoric acid is added to the dyebath, the fabric essentially loses no strength during the dyeing process. Thus, where the strength of the textile fabric must be maintained, and high coupling efficiencies of the dyestuff achieved, the use of the dyestuffs containing two or more phosphorus acid substituents is greatly preferred.

However, recent work has established that monophosponat dyestuffs can produce excellent fixation on substrates, using the process of the present invention, at a pH of about 5, To achieve thie pH, it is preferred to add about 0.125 to about 0.25 weight percent of phosphoric acid to the dye bath. Thus, broadly the amount of acid that can be used in the dyebath ranges from about 0.1 to about 5 weight percent.

Example 4 hereinabove relates to using a di(phosphorus acid)-substituted dyestuff. Additional examples of using such dyestuffs are set forth below.

EXAMPLE 17

H-acid (81% pure, 43.5g, 0.1 mole) of the formula:

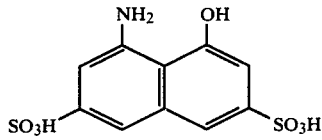

was suspended in 300 ml water and 100 g ice and the pH adjusted to 6 with sodium hydroxide solution. Sodium acetate (39 g, 0.3 mole) was added, followed by m-chlorosulfonylbenzenephosphonic acid (30 g, 0.12 mole) in portions over 10 minutes, the temperature being maintained at 10° C and the pH at 6. The solution was stirred for three hours in an ice bath, and then sodium carbonate (25 g) was added.

To this solution was added a diazotized solution of m-aminobenzenephosphonic acid. The combined solutions were stirred for 1 hour, then concentrated hydrochloric acid (400 ml) was added and the solution filtered to yield a red dye with the structure:

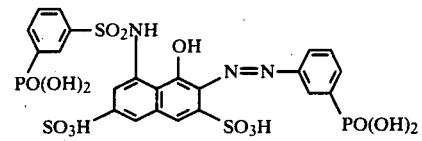

EXAMPLE 18

This and the following three examples relate to the production of orange dyes, using, as the starting compound, J acid of the formula:

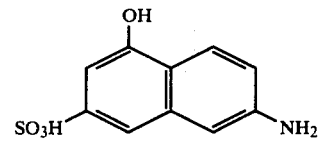

in place of the H acid. Example 17 was repeated, replacing the H acid with J acid, producing an orange dye of the formula:

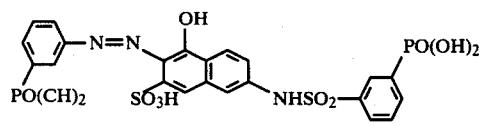

EXAMPLE 19

Example 18 was repeated, but using the N-methyl derivative of the J acid, to produce an orange dye of the formula:

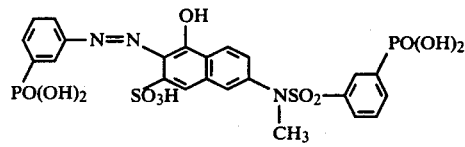

EXAMPLE 20

Example 18 was repeated, but the m-chlorosulfonylbenzenephosphonic acid was replaced by benzoylchloride, and the diazotized solution of m-aminobenzenephosphonic acid was replaced with a diazotized solution of o-amino-p-xylylenediphosphonic acid, to produce an orange dye of the formula:

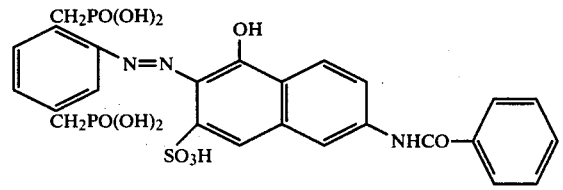

EXAMPLE 21

Example 19 was repeated, but the m-chlorosulphonylbenzenephosphonic acid waas deleted, and the diazotized solution of m-aminobenzenephosphonic acid was replaced with a diazotized solution of o-amino-p-xylylenediphosphonic acid, to produce an orange dye of the formula:

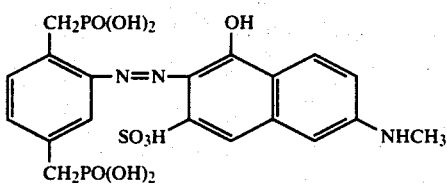

EXAMPLE 22

Following the procedure of Example 21, an orange dye was made by treating β-naphthol with diazotized o-amino-p-xylenediphosphonic acid, and the resulting dye had the formula:

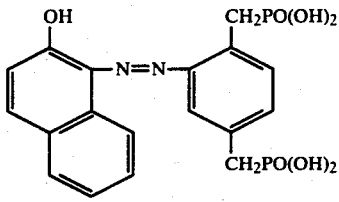

EXAMPLE 23

Example 22 was repeated, replacing the β-naphthol with F acid, of the formula:

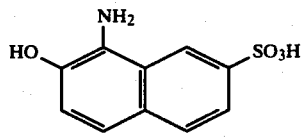

, resulting in an orange dye of the formula:

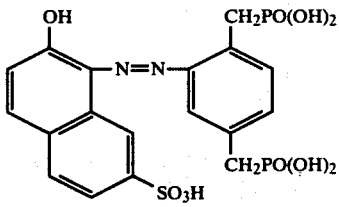

EXAMPLE 24

Bromaminic acid (89.9% pure, 132 g, 0.315 mole), p-amino benzylphosphonic acid (65 g, 0.345 mole), and cuprous chloride (12 g) were stirred in water (800 ml) and ethyl alcohol (200 ml), and sodium carbonate (160 g, 1.5 mole) added in portions. The solution was then heated to 50° C, and stirred at 45–50° C for 18 hours. The reaction mixture was cooled and poured carefully into concentrated hydrochloric acid (300 ml), and then filtered. The residue was recrystallized from aqueous hydrochloric acid to yield a blue dye of structure:

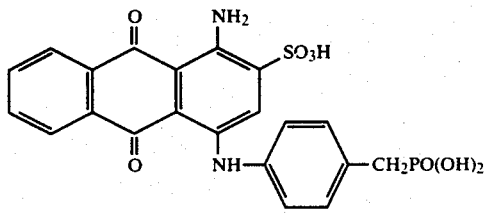

EXAMPLE 25

Example 24 was repeated, but the p-aminobenzylphosphonic acid was replaced by an equimolecular amount of o-amino-p-xylenediphosphonic acid, to produce a blue dye of the structure:

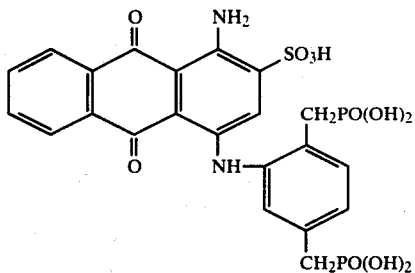

EXAMPLE 26 o-Amino-p-xylylenediphosphonic acid (28 g, 0.1 mole) was dissolved in water (150 ml) and sodium carbonate (21.2 g, 0.2 mole) added. Sodium nitrite (7.4 g, 0.107 mole) in water (40 ml) was added, and the solution was poured into a mixture of concentrated hydrochloric acid (50 ml) and ice (100 g). The solution was stirred at 5° for 20 minutes and then the excess nitrous acid destroyed with sulfamic acid. This solution was added to a solution of 3-methyl-1-(p-sulfophenyl)-2-pyrazolin-5-one (25.4 g, 0.1 mole) in water (300 ml) containing sodium carbonate (50 g), and stirred for 1 hour at 5° C. The solution was acidified with hydrochloric acid and from it was isolated the yellow dye:

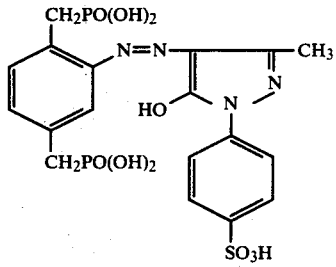

EXAMPLE 27

A pad bath was prepared containing 1% of the orange dye of Example 23, 2% of dimethylcyanamide (about 15 molar equivalents) and 0.1% Triton X100. Samples of a a multicomponent fabric containing discrete bands of wool, viscose rayon, silk, nylon, cotton, and Dacron were padded at 40 psi, oven dried for 2 minutes at 180° F and cured for 1.5 minutes at 390° F. The fabrics were washed in detergent, rinsed and dried. Under these conditions, the wool was only slightly tinted and the Dacron unaffected. The rayon and cotton were dyed bright orange, the nylon was dyed pink, and the silk was dyed a darker shade of orange than the cellulosic fibers.

EXAMPLE 28

An aqueous dye solution was made, with the solution containing 1% by weight of the orange dye of Example 18, 1% by weight of cyanamide, and 0.1% by weight of a surfactant (Triton X100). Rayon, nylon and wool fabrics were immersed in the dye solution, dried for five minutes at 180° F and cured for 90 seconds at 390° F.

After one home laundering the dyed samples showed significant dye fixation, with the rayon dyed the most strongly, followed, in order, by wool and nylon.

EXAMPLE 29

Separate aqueous dye solutions were prepared with each of the orange dyes of Examples 19. 20 and 23, each solution containing 1% by weight of the dye and 1% by weight of cyanamide. Separate cotton fabrics were then immersed in the respective dye solutions and then dried for five minutes at 180° F and thereafter cured for 90 seconds at 390° F. After one home laundering all of the dyed samples showed excellent dye fixation.

EXAMPLE 30

An aqueous dye solution was made with the solution containing 1% by weight of the yellow dye of Example 26 and 1% by weight of cyanamide. Cotton fabrics were immersed in this dye solution, dried for five minutes at 180° F and cured for 90 seconds at 390° F. After one home laundering the dyed samples wee a bright yellow color and had excellent dye fixation.

EXAMPLE 31

An aqueous dye solution was made, containing 0.5% by weight of the blue dye of Example 25 and 3% by weight of dicyandiamide, this solution having pH of 2. Cotton fabrics were immersed in the dye solution, dried for five minutes at 180° F and cured for 90 seconds at 390° F. After one home laundering the fabrics were dyed a bright blue and the dye fixation was excellent.

EXAMPLE 32

An aqueous dye solution was made containing 0.5% by weight of the blue dye of Example 25 and 1.25% by weight of cyanamide, the pH of said solution then being adjusted to a level of 3 by the addition of ammonium hydroxide. Cotton fabrics were immersed in the dye solution, dried for five minutes at 180° F and cured for 90 seconds. After one home laundering the fabrics were dyed bright blue and the dye fixation was excellent.

EXAMPLES 33 — 35

In a fashion generally similar to that of Example 28 above, cotton swatches were dyed in aqueous dye solutions prepared from each of the dyes of Example 21 (orange), 22 (orange) and 24 (blue). All of the dyed swatches showed excellent dye fixation after the home laundering.

COMPARATIVE EXAMPLE A

Example 28 was repeated, except the cyanamide was omitted. After one home laundering, the dyed fabrics were only tinted a very pale orange (an indication of little if any dye fixation).

Additional classes of phosphorus-containing dyes can be readily prepared, following the procedures of Examples 17 - 21 and 23, but replacing the H, J and F acids with the dye intermediates disclosed in U.S. Pat. Nos:
2,847,458
2,799,701
2,717,906
2,553,417 the disclosures of which are hereby incorporated by reference. Additional phosphorus-containing dyes which may be used in the practice of the present invention are disclosed in the following patents:

| | |
|---|---|
| Belgium | 563,439 |
| U.S. | 2,326,047 |
| U.S. | 3,339,999 |
| U.S. | 2,133,998 |
| U.S. | 3,202,550 |
| British | 970,585 |
| West German | 1042523 | the disclosures of which are hereby incorporated by reference.

Additional dyes which can be produced following the procedure of Example 21, but with different naphthylenic starting materials are of the formulae:

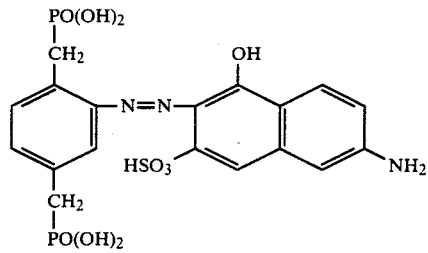

and

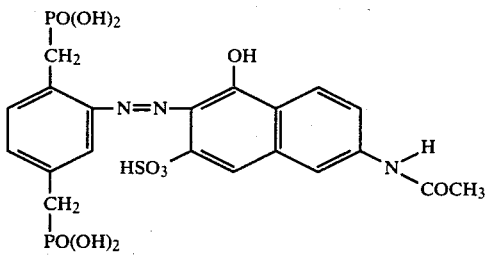

It is believed that the dyes of Examples 17, 18 and 19 are particularly novel. The results obtained with the dyes of these examples suggest that a new dye family of the class

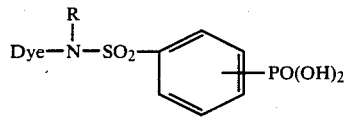

wherein R is hydrogen or lower alkyl, has been discovered. These dyes, especially those containing two or more phosphonate groups, work very well in the process of the present invention.

Of the various phosphorus-acid-substituted dyestuffs disclosed hereinabove, those dyestuffs substituted with more than one of said phosphorus acid radicals are particularly preferred, due to the excellent fixation obtained. In the latter regard, the dyes containing more than one phosphonate group have, as mentioned hereinabove, been found to be particularly preferred. The phosphonate substituents may be located at any point on the dye molecule, at generally proximate positions or at positions further removed from one another such as at the distal ends of the dye moiety.

Of the various phosphorus-acid-substituted dyestuffs disclosed hereinabove, those dyestuffs substituted with one or more phosphonate radicals are particularly preferred, due to the ease of dyeing and excellent durability obtained.

The results obtained hereinabove indicate that chromophore-substituted phosphorus acids broadly of the formula:

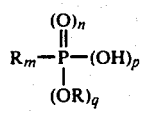

wherein each R is independently lower alkyl, aryl of 6 — 20 carbon atoms, aralkyl of 7 - 26 carbon atoms, alkaryl of 7 — 26 carbon atoms, or a chromophoric group, provided that at least one R is a chromophoric group, m is 0, 1 or 2, n is 0 or 1, p is 1 or 2, and q is 0 or 1, and $m + p + q = 3$ may be used in the process of the present invention. The chromophore-substituted phosphorus acids having hydrocarbon substituents on the oxygen atom (in addition to the chromophore) are not preferred, due to the decreased reactivity of these compounds, as well as the greater effort and expense in manufacturing same. However, it will be appreciated that such compounds may be used to replace part or all of the chromophore-substituted phosphonates or phosphates or similar compounds. Normally, only one chromophoric group will be attached to the phosphorus atom, either directly or indirectly (that is, it is preferred that the sum of m and q is 1, for both the formula of the preceding page and of page 7 hereinabove), that it is preferred, as indicated hereinabove, that the chromophoric group carry two or more phosphorus acid groups.

The present invention involves novel xylylene disphosphonic acid dyestuffs of the general formula

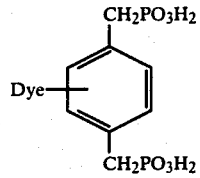

wherein Dye represents a chromophoric group, preferably an azoic chromophoric group. Such dyestuffs offer two potentially reactive sites when used in the process described herein, and thus generally result in high levels of fixation of the dyestuff on the substrate.

In addition to the preferred azoic chromophoric group, it will be readily appreciated by those in the art that other chromophoric groups may be utilized. For instance, Example 25 hereinabove relates to an anthraquinone chromophoric group, and Example 26 hereinabove relates to a pyrazoline chromophoric group. Clearly, any of the other chromophoric groups described hereinabove, or described in the references incorporated by reference hereinabove, could be substituted for the chromophoric groups disclosed herein in connection with the xylylene diphosphonic acid dyestuffs.

EXAMPLE 36

10 g of Procion Red NX2B (Reactive Red 1) were dissolved in 200-250 ml of water. One gram of m-amino benzene phosphonic acid(m-phosphanilic acid) was dissolved in 50 ml of water, using a small amount of caustic to aid solubilization. Then the phosphanilic acid solutiion was slowly added to the dye solution with stirring. The initial pH of the dye solution was 6.5, and this pH fell to 5.5 during the addition of the phosphanilic acid. The pH was adjusted to 6.8 with 50% caustic, and then the solution was warmed on a hot plate at 140° F for 20-30 minutes.

The resulting dye solution was cooled to room temperature and 15 g of phosphoric acid and 40 g of Cyanamide 50 (50% solution of cyanamide) were added, and the resulting solution was diluted to a total volume of 50 ml. The pH of the final solution was 1.7.

The dye solution was then padded on 100% cotton fabric at a pickup of 70%. The padded fabric was dried for two minutes at 220° F and cured for 45 seconds at 390° F in a Benz unit. The fabric ws scoured with a nonionic detergent and soda ash, and then subjected to five home launderings. The retention of color on the fabric was very good.

It is believed that the reaction between the Reactive Red 1 dyestuff and the phosphanilic acid was as follows:

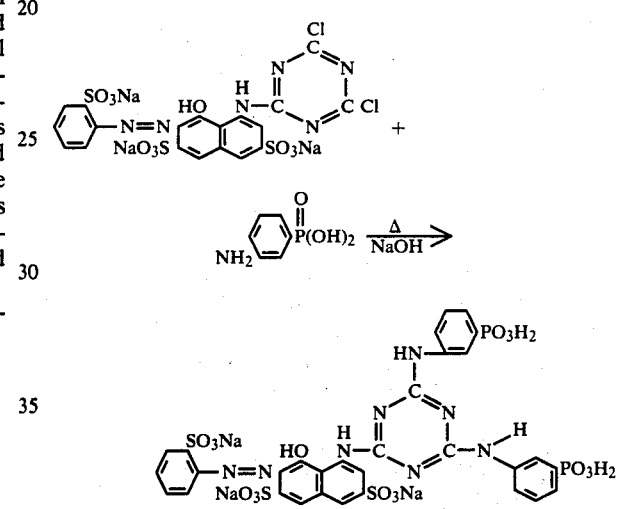

EXAMPLE 37

A reduced dye solution was prepared of a conventional monophosphate vat dye. A solution containing 5 grams per liter of the vat dye of the following formula:

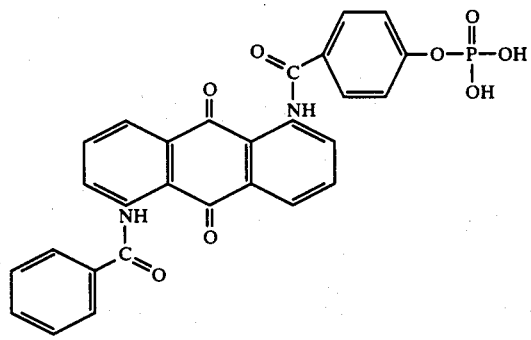

was reduced by the addition of 2 grams per liter of sodium hydro sulphite and, after the completion of the sodium hydro sulphite addition, 2 grams per liter of sodium hydroxide. The addition of the sodium hydroxide was accompanied by a color change, which would be expected for vat dyes, as denoting reduction of the dye to its soluble leuco form. Five grams per liter of a wetting agent (Igepal CO-710, obtained from GAF) was also added to the solution.

Immediately after preparation of the above reduced dye solution, a sample was padded onto 100% cotton, 3 ounce per yard sheeting, at a wet pickup of 75%. After padding, the sample was dried for 45 seconds at 220° F.

A portion of the fabric sample was rinsed in hot water (at approximately 180° F) containing 10 grams per liter of a scouring agent (Synthrapol (R)SP obtained from ICI). A portion of the rinsed sample was then washed five times according to AATCC test method 130-1970 II. The results are reported in Table 1 hereinbelow.

EXAMPLE 38

Example 37 was repeated, up through the padding of the cotton sheeting with the reduced dye solution. The sample was then padded a second time through a 5 gram per liter solution each of acetic acid and hydrogen peroxide. After the second padding step, the sample was dried for 45 seconds at 220° F. After this oxidizing step, the sample exhibited a color change, indicating that oxidation had occurred.

Portions of the sample were rinsed and washed by the procedure of Example 37, with the results reported at Table 1 below.

EXAMPLE 39

Example 37 was repeated, through the drying step of the padded cotton sheeting. After the drying step, the sample was padded through an aqueous solution containing 80 grams per liter of cyanamide and 10 grams per liter of phosphoric acid. The sample was then dried for 90 seconds at 390° F. This curing step allowed the reaction of the dye, the cyanamide and the cellulose to occur.

This sample was treated with the rinsing and washing treatment described in Example 37. The results are reported in Table 1 below.

EXAMPLE 40

Example 38 was repeated, but after the two padding steps and the drying step, the sample was padded through the cyanamide-phosphoric acid solution described in Example 39, and then cured at 390° F for 90 seconds.

This sample was rinsed and washed by the procedure of Example 37, and test results are described in TAble 1 hereinbelow.

TABLE 1

| Example | % Color After Rinse | % Color After 5 Washes |
|---|---|---|
| 37 Pad | 80.1 | 7.6 |
| 38 Pad ox. | 40.6 | 10.7 |
| 39 Pad/pad | 99.4 | 64.2 |
| 40 Pad/oxid/pad | 99.2 | 73.5 |

As shown in Table 1, there was some loss of color upon rinsing but the color loss was negligible for the samples of Examples 39 and 40. Washing resulted in even more dramatic differences between Examples 37 and 38, on the one hand, and 39 and 40, on the other. A definite depth of shade of the samples was readily apparent. The samples of Examples 37 and 38 showed almost complete loss of color. The samples of Examples 39 and 40, however, showed much less additional color loss after washing than the samples from experiments which did not utilize the cyanamide treatment. There was no substantial increase in color yield of the sample of Example 40 over the sample of Example 39, indicating that the chemical oxidation step had little positive effect on increasing the retention of the dye in the cellulose, with the oxidation resulting in about a 9% increase in color retention.

Examples 37 - 40 indicate that the after treatment of a dyed fabric with cyanamide, accompanied by a curing step, results in a more stable bond formation, and therefore a higher degree of fixation and dye retention in the fiber. The normal forces involved with vat dyes, including hydrogen bonding, van der Waals and other substantive-type bonds, were insufficient to retain suitable amounts of the dye in the fiber. In distinct contrast, the reaction between the dye, the cyanamide and the cellulose created a bond which was sufficiently strong to exhibit good dye retention.

EXAMPLE 41

Example 37 was repeated, using a corresponding amount of a monophosphonate dye of the following formula:

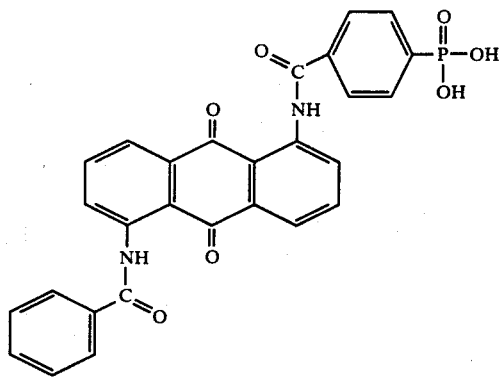

The results of evaluation of treated samples of this example are set forth in Table 2.

EXAMPLE 42

Example 38 was repeated, but using the monophosphonate dye of Example 41. The results of testing are set forth in Table 2 below.

EXAMPLE 43

Example 39 was repeated, but using the monophosphonate dye of Example 41. The results of testing are set forth in Table 2 below.

EXAMPLE 44

Example 40 was repeated, but using the monophosphonate dye of Example 41. The results of color retention testing are reported in Table 2 below.

TABLE 2

| Example | % Color After Rinse | % Color After 5 Washes |
|---|---|---|
| 41 | 38.8* | 9.6* |
| 42 | 64.5 | 13.6 |
| 43 | 89.2 | 64.0 |
| 44 | 95.2 | 71.8 |

*Average of two samples

The dyes used in Example 37 and in Example 41 were identical, except the phosphate group was replaced with the phosphonate group. The monophosphonate dye behaved in a similar manner to the monophosphate dye, with results almost identical. The results lead to basically the same conclusions as for Table 1, and also lead to the conclusion that the phosphate and phosphonate dyes behave in a similar manner in their reaction with cyanamide and cotton.

EXAMPLES 45 – 48

Examples 37 – 40 were repeated, but using a monophosphate vat dye of Example 13 of U.S. Pat. No. 3,339,999, which had the following formula:

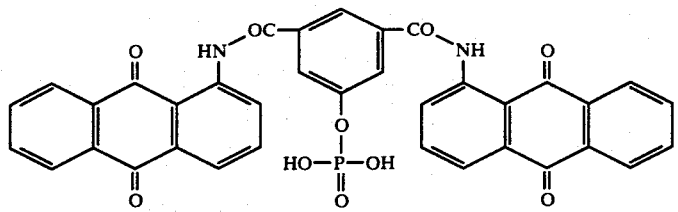

Examples 45 – 48 had experimental results similar to Examples 37 – 40.

EXAMPLES 49 – 52

Examples 37 – 40 were repeated, but using a diphosphate vat dye of Example 2 of U.S. Pat. No. 3,339,999, having the following formula:

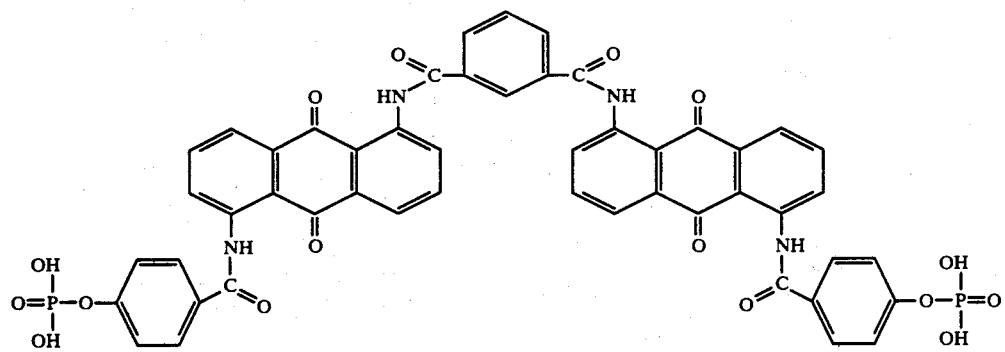

The results obtained for these examples were similar to the results obtained for examples 37 – 40.

EXAMPLES 53 – 56

Examples 37 – 40 were repeated, but using a diphosphate vat dye disclosed in Example 51 of U.S. Pat. No. 3,339,999, and having the following formula:

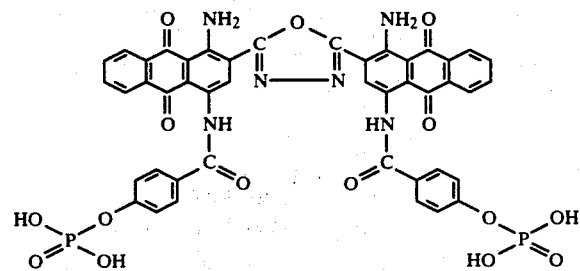

The experimental results on dyed samples of these examples were similar to the results obtained for Examples 37 – 40.

EXAMPLES 57 – 58

These examples relate to dyeings using a phosphate-containing dye which is not a vat dye, and therefore the necessity for having a reduction step is alleviated. The dyestuff used in these examples had the following structure:

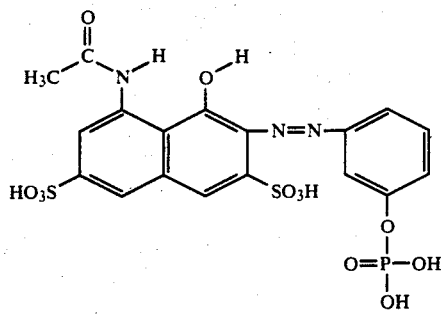

An aqueous pad dye bath solution was made, containing 0.5 weight percent of the above dye, 0.1 weight percent of wetting agent (Igepal CO-710), 1.0% of phosphoric acid, and 7% by weight of cyanamide, with all percentages based on the weight of the solution. Cotton samples were padded with the dye bath solution, using, in the case of Example 57, the dye bath solution described hereinabove, and, in the case of Example 58, the same solution but with the cyanamide and the phosphoric acid omitted.

The dyed samples of Example 57 (those containing the cyanamide and the phosphoric acid) had 73.7% color retention after rinsing, and 50.8% color retention after five washes, using the procedure of Example 37. On the other hand, Example 58, which used no cyanamide, showed practically no fixation (less than 10%).

EXAMPLES 59 – 60

Examples 57 – 58 were repeated, but using the phosphate-containing dye (which was not a vat dye) of the formula:

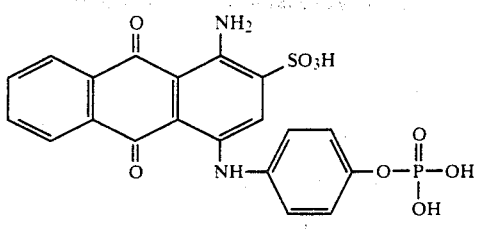

The cyanamide dye bath solution containd only 5% by weight of cyanamide, based on the weight of the solution. Example 59, which used the 5% by weight of cyanamide, and the phosphoric acid, resulted in 44.4% color retention after rinsing, and 39.3% color retention after five washes. On the other hand, Example 60, which corresponded to Example 58 in that it hd no cyanamide or phosphoric acid, resulted in little or no dye fixation.

It will be appreciated from Examples 37 – 56 hereinabove that a practical method has been developed for the application of phosphate vat dyes to cotton and cotton-containing fabrics, with good color fixation. The prior art to date was unable to use such vat dyes commercially on cotton, because of the problem of insufficient wash fastness.

EXAMPLE 61

Using the procedure of Example 24, a dyestuff was prepared of the following structural formula:

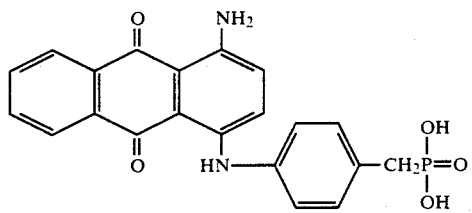

An aqueous dye bath solution was prepared, having 0.25 weight percent of the above dye, 2 weight percent of dicyandiamide, 0.1 weight percent of surfactant (Igepal CO 710) and 0.125 weight percent of phosphoric acid. A 100% cotton fabric was padded with this solution, passed through an oven at 400° F with an exposure time of 90 seconds, and then scoured using the procedure of Example 37 and measured colorimetrically for dye retention. About 78% of the original color was retained after scouring.

EXAMPLE 62

Example 61 was repeated, except that the dye bath contained 8 weight percent, based on the weight of the bath, of a 50% aqueous solution of cyanamide in addition to the 2 weight percent of dicyandiamide. About 87% color retention was obtained.

EXAMPLE 63

Example 61 was repeated, except the dicyandiamide was eliminated from the dyebath (that is, no dicyandiamide or cyanamide were in the dyebath). The color retention after scouring was about 10%, and even more color was removed upon laundering.

EXAMPLE 64

A printing paste was prepared using 0.15 weight percent of the dye of Example 25, and 0.05 weight percent of the dyestuff of the following formula:

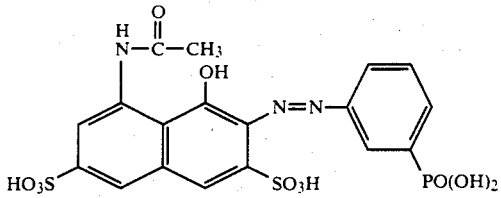

as well as 0.2 weight percent of wetting agent (Igepal C0-710)(nanylphenoxypoly(ethyleneoxy)ethanol having 10–11 ethyleneoxy units sold by GAF), 0.1 weight percent of $(NH_4)_2HPO_4$, 3.0 weight percent of dicyandiamide, 1.0 weight percent of sodium alginate, 33.0 weight percent of a 70% Varsol Emulsion, and balance water. All of the weight percents are based on the weight of the printing paste.

The prepared print paste has a pH of 8.6, and was screen printed on 100% cotton fabric at an add-on of about 5 grams per square yard (about a 100% average add-on). The fabric was dried and fixed at 400° F, at an exposure time of 60 seconds, to produce a printed cotton fabric having good color retention.

EXAMPLE 65

Another printing paste was prepared, based on 0.2 weight percent of the dye of Example 25, 0.05 weight percent of the dye having a structure as shown in Example 64, 0.2 weight percent of wetting agent (Igepal CO-710), 3.0 weight percent of dicyandiamide, 1.4 weight percent of sodium alginate, 15.0 weight percent of a 70% Varsol Emulsion, 1.0 weight percent of Carbowax 4000, and balance water. The printing paste had a pH of about 4.2. The paste was screen printed using the procedure of Example 4, with similar results.

As mentioned hereinabove, it is, in some instances, desirable to add an acid to the dyebath in order to adjust the pH to the desired level. Phosphoric acid is a convenient, strong acid which is preferred for such pH adjustment. However, other compounds can be used, including methyl acid phosphate, ammonium phosphate, boric acid, formic acid, lactic acid, glycolic acid and sulfuric acid.

It is preferred that the dye bath contain no solvent or dye assistant, but in certain instances the use of such auxiliary chemicals may be useful. If an organic solvent is used to assist in bringing the reactants of the present invention together at the reaction temperature (that is, the dye, the cyanamide compound, and the substrate), such a solvent should contain no free alcoholic-type hydroxyl group, should have a boiling point higher than that of water, and preferably should be miscible with water and the cyanamide compound. In such instances, suitable solvents might be Carbowx 350, Carbowax 750, Carbowax 2000, triethylene glycol diacetate, diethylene glycol diacetate or urea.

While a wide variety of chromophores may be used in the practice of the present invention, it is generally preferred that small dye molecules, compatible with color strength, be used. In general, long, linear dye molecules tend to position themselves along the cellulose polymer in such a manner that unreacted dye may be subjected to a slow release during subsequent washings, and not removed in adequate amounts during the production rinse.

Oarticularly preferred dyeing conditions for monophosphonic acid dyes include the use of about 0.2 weight percent surfactant, 0.2 weight percent phosphoric acid, no organic solvent dyeing assistant, 4.0% cyanamide and 3.0% dicyandiamide. Such a dyebath, with proper amounts of dyestuff therein, can be padded onto 100% cotton at about 75% pickup, and fixed at a temperature of about 390° F for about 90 seconds in a Benz unit. The color endurance of the dyed fabric (by color endurance, the percent color retention after a full production rinse and five AATCC washes is meant) runs about 75 – 90%, with less than 5% strength loss in the fabric tear strength and warp and fill tensile strengths.

The process of the present invention for the continuous dyeing of cotton equalsor exceeds other reactive dyeing systems now in use. The present process involves a pad-predry-bake-rinse-dry system which can be utilized on existing plant equipment. Most reactive dyeing systems are based upon alkaline dyeing environments, whereas the present system operates extremely well on the acid side with a pH of about 5, and thus is more compatible with the disperse dyes used in the thermosol dyeing of polyester-cotton fabrics. Dye migration problems can be controlled by normal adjustments in the padding and predrying steps in the operating plant, and such adjustments are even easier on polyester-cotton blends. The dyeings are quite consistently level. The strength loss of the cotton fabric is generally under 5%, which is about normal for reactive dyeing processing steps. The dyebaths of the present invention do not exhibit tailing (color strength loss) or ageing problems over a two-day period.

As mentioned above, the monophosphonic acid dyes used in the process of the present invention produce dyed fabrics having 70 – 90%, especially 75 – 90%, color endurance. This color endurance can be defined as the present color retained, compared to initial unrinsed fabric, after a full rinsing and five standard AATCC machine launderings. In contrast, the color endurance for competitive reactive dyes averages about 60 – 70%.

Previous attempts by the art to develop an acidside reactive dye system have been characterized by poor resistance to acid perspiration, whereas the fabrics dyed according to the present process showed little or no change in color, and little or no staining of a multifibered test fabric. Color loss resistance is excellent, ith the results from 10 – 25 washes looking very favorable. The light fastness of the dyed fabric of the present invention is at least competitive to other reactive dyes based on similar chromophores, and the same is true of similar tests, such as dry cleaning.

Another major advantage of the dye system of the present invention is that the present dyes are not subject to hydrolysis during storage, in distance contrast to the reactive dyestuffs which are now on the market, which have a restricted shelf like. The dyes of the present invention should last indefinitely under storage conditions, and this is basically because the present dyestuffs are stable to moisture attack, as compared to the commercially available reactive dyestuffs.

In other words, the dyes of the present invention are, in their original, unreacted state, simple acid dyes which are unaffected by moisture or water in any form. Thus, they will last with full efficiency for years, and this is in distinct contrast to reactive dyestuffs designed for alkaline-side dyeings.

Another major advantage of the dye systems of the present invention is the high percent fixation of the dye on the fiber which can be obtained. Normally, the alkaline-side reactive dyes have about 70% fixation or so, and fixations as high as 85% can be readily obtainable with the process of the present invention.

Yet a further major advantage of the dye systems of the present invention is the improved chlorine-type bleach resistance exhibited by the dyed fabrics. For instance, the dyed fabrics exhibit good resistance to the type of bleaches used in commercial laundries. After 5 cycles of the AATCC type IV-A test washes, the dyed fabrics of the present invention exhibit excellent color retention.

It is to be understood that only preferred embodiments of the invention have been described and that numerous alternatives, substitutions and modifications are all permissible without departing from the spirit or scope of the invention as defined in the following claims:

What is claimed is:

1. A reactive monoazo xylylene dyestuff of the formula

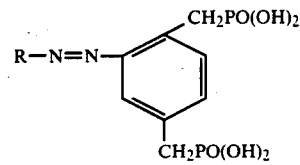

wherein R is a naphthyl ring having an —OH substituent ortho to the —N=N group, and, except for the —OH substituent, the naphthyl ring is either unsubstituted naphthyl, naphthyl substituted with —SO₃H or naphthyl substituted with —SO₃H and with a member selected from the group consisting of

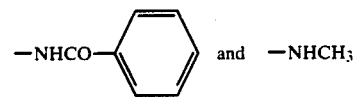

said dyestuff being characterized by the reactivity of its phosphonic acid groups with active hydrogen of the hydroxy groups of cellulose textile so that the chromophore can be fixed to the textile by condensation reaction through the P atom to form a cellulose phosphonic acid ester.

2. Dyestuff of claim 1 wherein said dyestuff has the formula:

3. Dyestuff of claim 1 wherein said dyestuff has the formula:

4. Dyestuff of claim 1 wherein said dyestuff has the formula:

[structure: 2-hydroxy-3-[(2,5-bis(phosphonomethyl)phenyl)azo]-6-(methylamino)naphthalene-... with SO₃H]

5. Dyestuff of claim 1 wherein said dyestuff has the formula:

[structure: 1-[(2,5-bis(phosphonomethyl)phenyl)azo]-2-naphthol]

6. Dyestuff of claim 1 wherein said dyestuff has the formula:

[structure: 1-[(2,5-bis(phosphonomethyl)phenyl)azo]-2-hydroxynaphthalene-6-sulfonic acid]

7. Dyestuff of claim 1 wherein said dyestuff has the formula:

[structure: pyrazolone azo dye with CH₂PO(OH)₂ groups and SO₃H]

* * * * *